United States Patent
Metten et al.

(10) Patent No.: US 9,072,685 B2
(45) Date of Patent: Jul. 7, 2015

(54) MEDIUM FOR THE TEMPORARY DEFORMATION OF KERATIN FIBRES AND METHOD FOR TEMPORARY HAIR DEFORMATION

(71) Applicant: Henkel AG & Co. KGaA, Dusseldorf (DE)

(72) Inventors: Diane Metten, Hamburg (DE); Bernd Richters, Hamburg (DE)

(73) Assignee: HENKEL AG & CO. KGAA, Dusseldorf (DE)

( * ) Notice: Subject to any disclaimer, the term of this patent is extended or adjusted under 35 U.S.C. 154(b) by 0 days.

(21) Appl. No.: 14/365,908

(22) PCT Filed: Nov. 9, 2012

(86) PCT No.: PCT/EP2012/072218
§ 371 (c)(1),
(2) Date: Jun. 16, 2014

(87) PCT Pub. No.: WO2013/087308
PCT Pub. Date: Jun. 20, 2013

(65) Prior Publication Data
US 2014/0341830 A1  Nov. 20, 2014

(30) Foreign Application Priority Data
Dec. 16, 2011 (DE) .......................... 10 2011 088 845

(51) Int. Cl.
*A61Q 5/06* (2006.01)
*A61K 8/81* (2006.01)
*A61K 8/34* (2006.01)

(52) U.S. Cl.
CPC ............... *A61K 8/8182* (2013.01); *A61Q 5/06* (2013.01); *A61K 8/8129* (2013.01); *A61K 8/8152* (2013.01); *A61K 2800/594* (2013.01); *A61K 8/345* (2013.01)

(58) Field of Classification Search
CPC ..... A61Q 5/06; A61K 8/8129; A61K 8/8182; A61K 8/8152; A61K 2800/594
USPC .......................... 424/70.1, 70.15, 70.16, 70.2
See application file for complete search history.

(56) References Cited

U.S. PATENT DOCUMENTS

2010/0028272 A1* 2/2010 Knappe et al. .................. 424/47

FOREIGN PATENT DOCUMENTS

| WO | 9913841 A1 | 3/1999 | |
|---|---|---|---|
| WO | 2012075274 A1 | 6/2012 | |
| WO | WO 2013/056888 | * 4/2013 | ............... A61Q 5/06 |

OTHER PUBLICATIONS

STIC Search Report dated Oct. 17, 2014.*
International Search Reported completed Jun. 18, 2013 in PCT/EP2012/072218.
"ISP launches Styleze XT3, latest polymer technology to protect hair from heat," Internet Citation, Apr. 1, 2011, http://www.specialchem4cosmetics.com/services/news.aspx?id=6408.
"Styleze XT3 polymer," Internet Citation, 2012, http://www.ashland.com/products/styleze-x13-polymer.

* cited by examiner

*Primary Examiner* — Eisa Elhilo
(74) *Attorney, Agent, or Firm* — Ingrassia Fisher & Lorenz, P.C.

(57) ABSTRACT

Cosmetic agents, containing in a cosmetically acceptable carrier a) at least one copolymer A with at least one structural unit (A1), at least one structural unit (A2), at least one structural unit (A3) and at least one structural unit (A4), wherein—R1 denotes an optionally heterofunctionalized alkyl residue;—R2 denotes an optionally heterofunctionalized alkyl residue differing from R1;—R3 denotes an optionally heterofunctionalized alkyl residue mutually independently differing from R1 and R2 b) at least one copolymer B differing from copolymer A with at least one structural unit (B1), wherein R4 denotes an optionally heterofunctionalized alkyl residue; and c) at least one copolymer C differing from copolymer A and copolymer B, prepared from—at least one monomer C1 selected from acrylic acid, methacrylic acid, acrylic acid alkyl ester and methacrylic acid alkyl ester, and at least one amphoteric monomer C2 selected from (meth)acryloyl alkyl amine oxides of formula C2-I and (meth)acryloyl alkyl betaines of formula C2-II, wherein in formula C2-I and in formula C2-II $R^1$ denotes H or $CH_3$, $R^2$ and $R^3$ in each case mutually independently denote optionally branched $C_{1-10}$ alkyl and n denotes an integer from 1 to 20, are particularly suitable for temporarily deforming keratinic fibers.

16 Claims, No Drawings

MEDIUM FOR THE TEMPORARY DEFORMATION OF KERATIN FIBRES AND METHOD FOR TEMPORARY HAIR DEFORMATION

CROSS REFERENCE TO RELATED APPLICATIONS

The present disclosure is a U.S. National Stage entry under 35 U.S.C. §371 based on International Application No. PCT/EP2012/072218, filed Nov. 9, 2012 which was published under PCT Article 21(2) and which claims priority to German Patent Application No. DE 10 2011 088 845.4 filed on Dec. 16, 2011, which is incorporated herein by reference in its entirety.

TECHNICAL FIELD

The technical field describes cosmetic agents based on a specific polymer combination, use of these cosmetic agents for temporarily deforming keratinic fibers and cosmetic methods using these agents.

BACKGROUND

Polymers are widely used in the most varied cosmetic agents. They are to be found in agents for treating skin as well as in agents for treating hair, in agents which are washed off or out again directly after use, i.e. "rinse-off products", and in agents which remain on the skin or hair, i.e. "leave-on agents". The polymers are used for the most varied reasons and specific properties of the polymers are exploited in each case. In agents for treating skin, in shampoos, hair rinses and hair masks, the emphasis often lies on the thickening or conditioning properties of the polymers. In agents for temporarily deforming keratinic fibers, hereinafter also known as styling agents, alongside these properties film-forming and/or setting effects are particularly desired. Polymers often also serve as auxiliaries for improving or indeed enabling deposition and fixing of other active substances and ingredients on the skin or hair. By adding suitable polymers to hair coloring agents, for example, rubbing fastness and coloring durability may be increased.

Cosmetic agents generally contain individual polymers which are specifically tailored to achieving a very specific effect. If various effects are to be achieved, a plurality of polymers must be added. However, using too many different polymers may be associated with a series of disadvantages. Problems may accordingly arise during formulation, for instance because the polymers react with one another or with other components of the agent resulting in precipitation or decomposition phenomena. Certain polymers also have a tendency to be deposited so permanently on the skin and in particular on the hair that they are no longer completely removed with normal washing and the polymer accumulates undesirably so ultimately leading to contamination of the skin or hair.

There is therefore a constant need for polymers or suitable combinations of small numbers of polymers which simultaneously exhibit as many as possible of the desired properties.

For example, in the case of styling agents, the polymers used need to give the treated hair the strongest possible hold. In addition to a high degree of hold, styling agents must meet a whole series of further requirements. These may be broadly divided into properties on the hair, properties of the respective formulation, for example properties of the foam, the gel or the sprayed aerosol, and properties which affect the handling of the styling agent, wherein properties on the hair are of particular importance. Particular mention should be made of moisture resistance, low tackiness and a well-balanced conditioning effect. Moreover, a styling agent should as far as possible be universally applicable for all hair types. If the styling agent is a gel or a paste, the polymers should additionally have thickening properties.

SUMMARY

The object of the present invention was accordingly to provide further suitable polymer combinations which are distinguished by good film-forming and/or setting properties, have a very high level of hold without having to sacrifice flexibility and good moisture resistance, in particular perspiration and water resistance, and are additionally suitable for producing stably viscous and stably transparent cosmetic compositions.

An exemplary embodiment provides a cosmetic agent, containing in a cosmetically acceptable carrier
a) at least one copolymer A with at least one structural unit (A1), at least one structural unit (A2), at least one structural unit (A3) and at least one structural unit (A4),

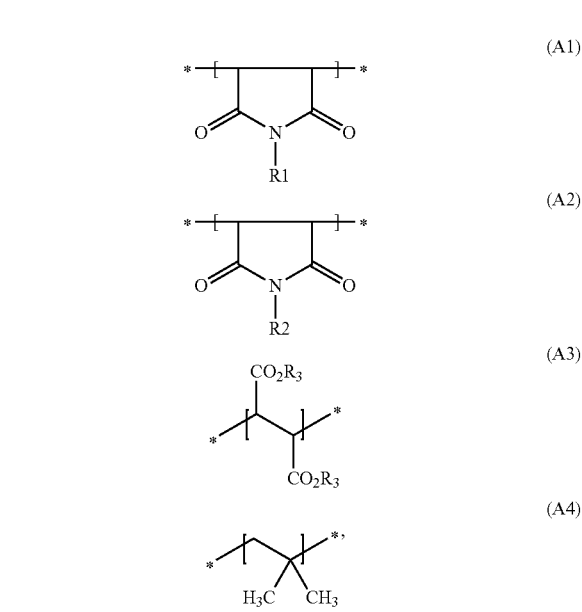

wherein
R1 denotes an optionally heterofunctionalized alkyl residue;
R2 denotes an optionally heterofunctionalized alkyl residue differing from R1;
R3 denotes an optionally heterofunctionalized alkyl residue mutually independently differing from R1 and R2;
b) at least one copolymer B differing from copolymer A with at least one structural unit (B1)

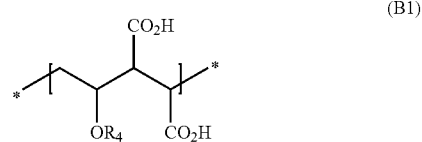

wherein $R^4$ denotes an optionally heterofunctionalized alkyl residue; and
c) at least one copolymer C differing from copolymer A and copolymer B, prepared from
at least one monomer C1 selected from acrylic acid, methacrylic acid, acrylic acid alkyl esters and methacrylic acid alkyl esters, and
at least one amphoteric monomer C2 selected from (meth)acryloyl alkyl amine oxides of formula C2-I

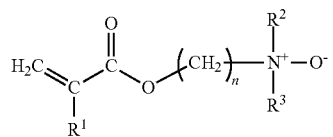

C2-I and (meth)acryloyl alkyl betaines of formula C2-II

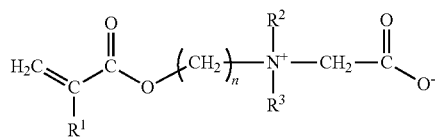

C2-II wherein in formula C2-I and in formula C2-II
$R^1$ denotes H or $CH_3$,
$R^2$ and $R^3$ in each case mutually independently denote optionally branched $C_{1-10}$ alkyl and
n denotes an integer from 1 to 20.

The agents according to the invention contain the active substances in a cosmetic carrier. This cosmetic carrier is aqueous, alcoholic or aqueous-alcoholic. For the purposes of the present invention, aqueous-alcoholic carriers should be taken to be hydrous compositions containing from about 3 to about 70 wt. % of a $C_1$-$C_4$ alcohol, in particular ethanol or isopropanol, relative to the total weight of the mixture for use. For the purposes of the invention, an aqueous carrier contains at least about 30 wt. %, in particular at least about 50 wt. % water, relative to the total weight of the mixture for use. Preferred cosmetic agents contain, relative to the total weight thereof, from about 40 to about 99 wt. %, preferably from about 50 to about 98 wt. %, more preferably from about 60 to about 95 wt. % and in particular from about 70 to about 90 wt. % water. Particularly preferred cosmetic agents comprise from about 60 to about 99 wt. %, preferably from about 75 to about 98 wt. % and in particular from about 85 to about 95 wt. % water and from about 0.1 to about 20 wt. %, preferably from about 0.5 to about 10 wt. % and in particular from about 1.0 to about 7.0 wt. % $C_1$-$C_4$ alcohol, preferably ethanol.

The agents according to the invention contain as first essential component a copolymer A, comprising the structural units (A1), (A2), (A3) and (A4). With regard to the technical effect of the agents according to the invention, it has proven advantageous for copolymer A to consist in a proportion of at least about 70 wt. %, preferably at least about 80 wt. %, preferably at least about 90 wt. % and in particular of at least about 95 wt. % of structural units (A1), (A2), (A3) and (A4). Further preferred copolymers A consist completely of structural units (A1), (A2), (A3) and (A4).

In one preferred embodiment, the residue $R^1$ in structural unit (A1) denotes an ether residue, preferably a polyalkoxylated residue. Structural units (A1) which are more preferred are those in which R1 in formula (A1) denotes a residue —$CH(CH_3)CH_2$—$(OCH(CH_3)CH_2)_x(O[CH_2]_2)_yOCH_3$, in which x and y mutually independently have a value between 1 and 100.

The residue R2 in the structural unit (A2) preferably denotes an amino group-containing residue, preferably a residue with a tertiary amine Structural units (A2) which are more preferred are those in which R2 in formula (A2) denotes a residue —$(CH_2)_3$—$N(CH_3)_2$.

In structural unit (A3) preferably at least one alkyl residue, preferably a $C_1$ to $C_4$ alkyl residue is used as residue R3. Structural units (A3) which are more preferred are those in which R3 denotes —$CH_2CH_3$ or —$CH_2CH_2CH_3$, preferably —$CH_2CH_3$ and a residue R3 in formula (A3) denotes H.

Some preferred copolymers A are listed below. These copolymers A consist in a proportion of at least about 70 wt. %, preferably of at least about 80 wt. %, preferably of at least about 90 wt. % and in particular of at least about 95 wt. %, particularly preferably completely of structural units (A1), (A2), (A3) and (A4):
A-I) copolymer A with at least one structural unit (A1), at least one structural unit (A2), at least one structural unit (A3) and at least one structural unit (A4),

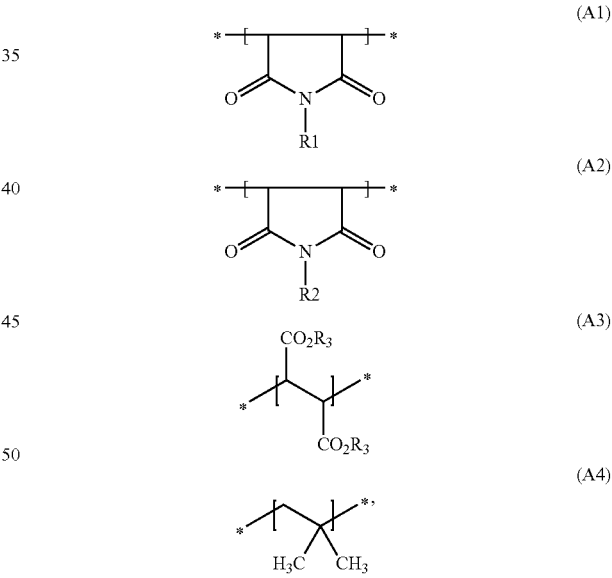

wherein
R1 in formula (A1) denotes a residue —$CH(CH_3)CH_2$—$(OCH(CH_3)CH_2)_x(O[CH_2]_2)_yOCH_3$, in which x and y mutually independently have a value between 1 and 100;
R2 in formula (A2) denotes a residue —$(CH_2)_3$—$N(CH_3)_2$;
R3 denotes an optionally heterofunctionalized alkyl residue mutually independently differing from R1 and R2.
A-II) copolymer A with at least one structural unit (A1), at least one structural unit (A2), at least one structural unit (A3) and at least one structural unit (A4),

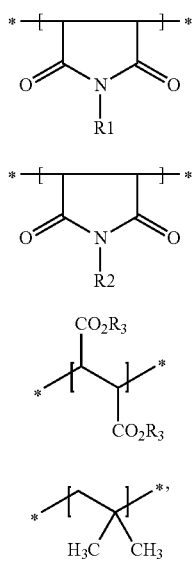

wherein
R1 in formula (A1) denotes a residue —CH(CH$_3$)CH$_2$—(OCH(CH$_3$)CH$_2$)$_x$(O[CH$_2$]$_2$)$_y$OCH$_3$, in which x and y mutually independently have a value between 1 and 100;
R2 denotes an optionally heterofunctionalized alkyl residue differing from R1;
a residue R3 in the formula (A3) denotes —CH$_2$CH$_3$ or —CH$_2$CH$_2$CH$_3$, preferably —CH$_2$CH$_3$ and a residue R3 in formula (A3) denotes H.
A-III) copolymer A with at least one structural unit (A1), at least one structural unit (A2), at least one structural unit (A3) and at least one structural unit (A4),

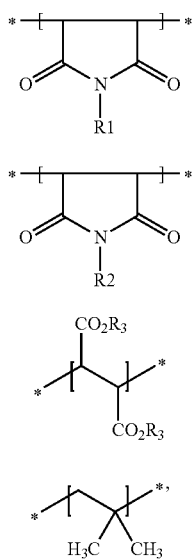

wherein
R1 denotes an optionally heterofunctionalized alkyl residue;
R2 in formula (A2) denotes a residue —(CH$_2$)$_3$—N(CH$_3$)$_2$;
a residue R3 in the formula (A3) denotes —CH$_2$CH$_3$ or —CH$_2$CH$_2$CH$_3$, preferably —CH$_2$CH$_3$ and a residue R3 in formula (A3) denotes H.

Particularly preferred cosmetic agents according to the invention are characterized in that
the residue R1 in formula (A1) denotes a residue —CH(CH$_3$)CH$_2$—(OCH(CH$_3$)CH$_2$)$_x$(O[CH$_2$]$_2$)$_y$OCH$_3$, in which x and y mutually independently have a value of between 1 and 100;
the residue R2 in formula (A2) denotes a residue —(CH$_2$)$_3$—N(CH$_3$)$_2$;
one residue R3 denotes —CH$_2$CH$_3$ and one residue R3 in formula (A3) denotes H.

The proportion by weight of copolymer A in the total weight of cosmetic agents according to the invention preferably amounts to from about 0.05 to about 10 wt. %, preferably from about 0.1 to about 7.0 wt. % and in particular from about 0.2 to about 5.0 wt. %.

As their second essential component, the agents according to the invention contain a copolymer B, comprising the structural unit (B1). With regard to the technical effect of the agents according to the invention, it has proven advantageous for copolymer B to consist in a proportion of at least about 70 wt. %, preferably at least about 80 wt. %, preferably at least about 90 wt. % and in particular at least about 95 wt. % of structural unit (B1). Further preferred copolymers B consist completely of structural unit (B1).

In a preferred embodiment, the residue R4 in the structural unit (B1) denotes an alkyl residue, preferably a $C_1$ to $C_4$ alkyl residue. The structural unit (B1) in which residue R4 denotes —CH$_3$ is more preferred.

The proportion by weight of copolymer B in the total weight of a cosmetic agent according to the invention preferably amounts to from about 0.05 to about 10 wt. %, preferably from about 0.1 to about 7.0 wt. % and in particular from about 0.2 to about 5.0 wt. %.

Copolymers A and B may be incorporated into the agent according to the invention in pure form. For processing and the cosmetic properties of the cosmetic agents according to the invention, however, it has proven advantageous to use copolymers A and B in pre-formulated form, i.e. in combination with further active or auxiliary substances. In particular, mixtures of copolymers A and B are preferably used. The weight ratio of copolymer A to copolymer B in the polymer mixtures preferably used amounts to about 20:1 to about 1:20, preferably about 10:1 to about 1:10, in particular about 8:1 to about 1:8 and particularly preferably about 5:1 to about 1:5. Consequently, cosmetic agents according to the invention are therefore also preferred in which the weight ratio of copolymer A to copolymer B amounts to about 20:1 to about 1:20, preferably about 10:1 to about 1:10, in particular about 8:1 to about 1:8 and particularly preferably about 5:1 to about 1:5. The use of copolymers A and B in a weight ratio of about 2:1 to about 1:4, preferably of about 1:1 to about 1:3 is particularly preferred, with copolymer B preferably being used in excess.

The previously described copolymers A and B or mixtures thereof are preferably combined with additional auxiliary substances. The use of alcohols is more preferred. A preferred class of alcohols is diols, in particular 1,2-diols. 1,2-Octanediol is particularly preferentially used. In particular, 1,2-octanediol not only simplifies further processing of copolymers A and B, or mixtures thereof, but also enhances the advantageous technical effect thereof, in particular the conditioning effect thereof.

The above-stated diols may be incorporated into the cosmetic agents according to the invention together with copolymers A and B, or mixtures thereof, or separately from copolymers A and B. Against this background, preferred cosmetic agents according to the invention are those which additionally contain at least one 1,2-diol, preferably 1,2-octanediol.

A polymer mixture preferred according to the invention based on copolymers A and B is distributed by ISP under the name Styleze® XT3 (INCI: Water (and) Polyimide-1 (and) PVM/MA Copoylmer (and) Caprylyl Glycol (proposed)).

The agents according to the invention contain as third essential component a copolymer C based on the monomers C1 and C2. For the technical effect of the agents according to the invention, agents have proven advantageous in which the copolymer C consists in a proportion of at least about 70 wt. %, preferably of at least about 80 wt. %, preferably of at least about 90 wt. % and in particular of at least about 95 wt. % of the monomers C1 and C2. Further preferred copolymers C consist completely of the monomers C1 and C2.

Preferred monomers C1 are acrylic acid, methacrylic acid, acrylic acid $C_{1-20}$ alkyl esters and methacrylic acid $C_{1-20}$ alkyl esters.

Monomer C1 is more preferably selected from acrylic acid, methacrylic acid, methyl acrylate, methyl methacrylate, ethyl acrylate, ethyl methacrylate, propyl acrylate, propyl methacrylate, isopropyl acrylate, isopropyl methacrylate, lauryl acrylate, lauryl methacrylate, cetyl acrylate, cetyl methacrylate, stearyl acrylate and stearyl methacrylate, particularly preferably from acrylic acid, methacrylic acid, methyl acrylate, methyl methacrylate, ethyl acrylate, ethyl methacrylate, lauryl acrylate, lauryl methacrylate, stearyl acrylate and stearyl methacrylate.

Preferred monomers C2 are (meth)acryloyl alkyl amine oxides of formula C2-I and/or (meth)acryloyl alkyl betaines of formula C2-II, wherein R2 and R3 in each case mutually independently denote methyl, ethyl, propyl, isopropyl, butyl, isobutyl or tert-butyl, more preferably methyl.

Preferred monomers C2 are furthermore selected from at least one monomer from the group formed of (meth)acryloyl alkyl amine oxides of formula C2-I and/or (meth)acryloyl alkyl betaines of formula C2-II, wherein n in each case denotes an integer from 1 to 5, preferably an integer from 1 to 3 and more preferably 2.

Preferred monomers C2 are also those which are selected from at least one monomer from the group formed from (meth)acryloyl alkyl amine oxides of formula C2-I and/or (meth)acryloyl alkyl betaines of formula C2-II, wherein R1 in each case denotes $CH_3$.

More preferred monomers C2 are those which are selected from at least one monomer from the group formed of (meth)acryloyl alkyl amine oxides of formula C2-I and/or (meth)acryloyl alkyl betaines of formula C2-II, wherein R2 and R3 in each case mutually independently denote methyl, ethyl, propyl, isopropyl, butyl, isobutyl or tert.-butyl, more preferably methyl, n in each case denotes an integer from 1 to 5, preferably an integer from 1 to 3 and more preferably 2, and R1 in each case denotes $CH_3$.

Monomer C2 is particularly preferably selected from at least one monomer from the group formed of (meth)acryloyl alkyl amine oxides of formula C2-I and/or (meth)acryloyl alkyl betaines of formula C2-II, wherein R1, R2 and R3 in each case denote $CH_3$ and n denotes 2.

In all the above-described embodiments, it is in turn preferable for the copolymer C to be formed (in particular exclusively) from at least one monomer of formula C1 and at least one monomer of formula C2-I corresponding to the respective embodiment.

In one preferred embodiment, the agent according to the invention contains at least one copolymer C, formed from
at least one monomer C1 selected from acrylic acid, methacrylic acid, methyl acrylate, methyl methacrylate, ethyl acrylate, ethyl methacrylate, propyl acrylate, propyl methacrylate, isopropyl acrylate and isopropyl methacrylate, and
methacryloyl ethyl betaine as monomer C2.

Corresponding copolymers are known and obtainable for example from Clariant under the names Diaformer Z-400, Diaformer Z-AT, Diaformer Z-301N, Diaformer Z-SM and Diaformer Z-W and from Mitsubishi under the names Yukaformer 202, Yukaformer 204, Yukaformer 206 and Yukaformer 301, wherein the use of Diaformer Z-301N is more preferred.

In one more preferred embodiment, the agent according to the invention contains at least one copolymer C, which is formed from
at least two monomers C1, wherein the first monomer is selected from acrylic acid, methacrylic acid, methyl acrylate, methyl methacrylate, ethyl acrylate, ethyl methacrylate, propyl acrylate, propyl methacrylate, isopropyl acrylate and isopropyl methacrylate, and the second monomer is selected from stearyl acrylate and stearyl methacrylate, and
methacryloyl ethylamine oxide, in particular methacryloyl ethyl-N,N-dimethylamine oxide as monomer C2 (in the formula C2-I: $R^1$=$CH_3$, n=2, $R^2$ and $R^3$=$CH_3$).

These copolymers are also known and obtainable for example from Clariant under the name Diaformer Z-632, wherein the use of Diaformer Z-632 is more preferred.

In one preferred embodiment, the agent according to the invention contains at least one copolymer C, formed from
at least three monomers C1, wherein the first monomer is selected from acrylic acid, methacrylic acid, methyl acrylate, methyl methacrylate, ethyl acrylate, ethyl methacrylate, propyl acrylate, propyl methacrylate, isopropyl acrylate and isopropyl methacrylate, the second monomer is selected from stearyl acrylate and stearyl methacrylate, and the third monomer is selected from stearyl acrylate and stearyl methacrylate, and
methacryloyl ethylamine oxide, in particular methacryloyl ethyl-N,N-dimethylamine oxide as monomer C2 (in the formula C2-I: $R^1$=$CH_3$, n=2, $R^2$ and $R^3$=$CH_3$).

Corresponding copolymers are likewise known and obtainable for example from Clariant under the names Diaformer Z-611, Diaformer Z-612, Diaformer Z-613, Diaformer Z-631, Diaformer Z-633, Diaformer Z-651, Diaformer Z-711N, Diaformer Z-712N and Diaformer Z-731N, wherein the use of Diaformer Z-712N and Diaformer Z-651 is preferred.

It goes without saying that it is also possible for the agents according to the invention to contain a mixture of at least two of copolymers C, which are used according to the three preferred embodiments just described. The proportion by weight of copolymer C in the total weight of cosmetic agent according to the invention preferably amounts to about 0.1 to about 8.0 wt. %, preferably about 0.2 to about 6.0 wt. % and in particular about 0.4 to about 4.0 wt. %.

The agents according to the invention are distinguished from cosmetic agents with alternative copolymers C not only by the above-stated advantages but in particular also by an improved level of hold. For the cosmetic properties of the agents according to the invention, a ratio of the joint proportions by weight of copolymers A and B to the proportion by weight of polymer C in the cosmetic agent between about 8:1 and about 1:8, preferably between about 6:1 and about 1:6 and in particular between about 4:1 and about 1:4 has proven particularly advantageous.

The copolymers A, B and C are used in the cosmetic agents preferably in partially neutralized or neutralized form. At least one alkanolamine is preferably used for neutralization. The alkanolamines usable as an alkalizing agent according to the invention are preferably selected from primary amines with a $C_2$-$C_6$ alkyl parent substance which bears at least one hydroxyl group. More preferred alkanolamines are selected from the group formed from 2-aminoethan-1-ol (monoethanolamine), tris(2-hydroxyethyl)amine(triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Alkanolamines which are particularly preferred according to the invention are selected from the group 2-aminoethan-1-ol, 2-amino-2-methylpropan-1-ol and 2-amino-2-methylpropane-1,3-diol. 2-Amino-2-methylpropanol has proven to be a particularly suitable neutralizing agent. Cosmetic agents which are preferred according to the invention therefore contain 2-amino-2-methylpropanol. 2-Amino-2-methylpropanol is used in the agents according to the invention preferably in a quantity which does not exceed the quantity needed to neutralize copolymers A, B and C. The quantities of 2-amino-2-methylpropanol used in the agents according to the invention preferably amounts to about 80 to about 100%, more preferably about 90 to about 100% and in particular about 95 to about 100% of the quantity required for complete neutralization of the copolymers A, B and C. In a preferred embodiment, the proportion by weight of 2-amino-2-methylpropanol in the total weight of the cosmetic agent amounts to about 0.1 to about 4.0 wt. %, preferably about 0.2 to about 3.0 wt. % and in particular about 0.5 to about 2.0 wt. %.

In addition to the previously described copolymers and carrier substances, the cosmetic agents according to the invention may contain further ingredients. The group of these further ingredients in particular includes cosmetically active auxiliary substances and additives.

The cosmetic agents according to the invention contain as preferred component at least one quaternary ammonium compound. Monomeric or polymeric active substances may be used as the quaternary ammonium compound.

From the plurality of possible monomeric quaternary ammonium compounds, the compounds from the groups:
trimethylalkylammonium halides;
ester quats
quaternary imidazolines have proven particularly effective.

The group of trimethylalkylammonium halides in particular includes the compounds of formula (Tkat1-1).

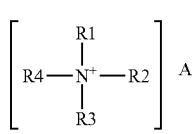

(Tkat 1)

In the formula (Tkat1), R1, R2, R3 and R4 in each case mutually independently denote hydrogen, a methyl group, a phenyl group, a benzyl group, a saturated, branched or unbranched alkyl residue with a chain length of 8 to 30 carbon atoms, which may optionally be substituted with one or more hydroxyl groups. A denotes a physiologically acceptable anion, for example halides such as chloride or bromide and methosulfates. Examples of compounds of formula (Tkat1) are lauryltrimethylammonium chloride, cetyltrimethylammonium chloride, cetyltrimethylammonium bromide, cetyltrimethylammonium methosulfate, dicetyldimethylammonium chloride, tricetyl-methylammonium chloride, stearyltrimethylammonium chloride, distearyl-dimethylammonium chloride, lauryldimethylbenzylammonium chloride, behenyl-trimethylammonium chloride, behenyltrimethylammonium bromide and behenyl-trimethylammonium methosulfate. Preferred cosmetic agents contain a monomeric quaternary ammonium compound from the group of trimethylalkylammonium halides.

Further quaternary ammonium compounds which are more preferred according to the invention are the cationic betaine esters of formula (Tkat1-2.1).

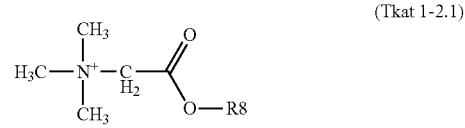

(Tkat 1-2.1)

More preferred ester quats are those with the trade names Armocare VGH-70, and Dehyquart® F-75, Dehyquart® L80, Stepantex® VS 90 and Akypoquat® 131.

A further group are quaternary imidazoline compounds. The formula (Tkat2) illustrated below shows the structure of these compounds.

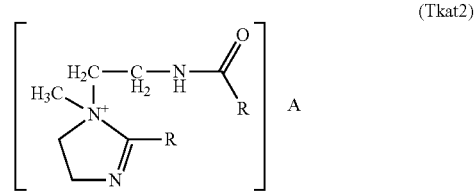

(Tkat2)

The residues R mutually independently in each case denote a saturated or unsaturated, linear or branched hydrocarbon residue with a chain length of 8 to 30 carbon atoms. The preferred compounds of the formula (Tkat2) in each case contain the identical hydrocarbon residue for R. The chain length of the residues R preferably amounts to 12 to 21 carbon atoms. A denotes an anion as previously described. Examples which are particularly according to the invention are obtainable for example under INCI names Quaternium-27, Quaternium-72, Quaternium-83, Quaternium-87 and Quaternium-91. Quaternium-91 is most preferred according to the invention.

With regard to cosmetic action, advantageous cosmetic agents have proven to be those in which the proportion by weight of the monomeric quaternary ammonium compound in the total weight of the agent amounts to about 0.05 to about 3.0 wt. %, preferably about 0.1 to about 2.0 wt. % and in particular about 0.2 to about 1.0 wt. %.

Suitable auxiliary substances and additives which may be mentioned are in particular additional conditioning substances. An example of a conditioning substance which may be used is a silicone oil and/or a silicone gum.

Silicone oils or silicone gums suitable according to the invention are in particular dialkyl- and alkylarylsiloxanes, such as for example dimethylpolysiloxane and methylphenylpolysiloxane, and the alkoxylated, quaternized or also anionic derivatives thereof. Preference is given to cyclic and linear polydialkylsiloxanes, the alkoxylated and/or aminated derivatives thereof, dihydroxypolydimethylsiloxanes and polyphenylalkylsiloxanes.

The agent may for example contain at least one protein hydrolysate and/or one of the derivatives thereof as a conditioning substance of another compound class. Protein hydrolysates are product mixtures which are obtained by acidically, basically or enzymatically catalyzed degradation of proteins. According to the invention, the term protein hydrolysates also covers total hydrolysates and individual amino acids and the derivatives thereof and mixtures of different amino acids. The molecular weight of the protein hydrolysates which may be used according to the invention is from about 75, the molecular weight of glycine, to about 200,000, the molecular weight preferably amounting to from about 75 to about 50,000 and particularly preferably to from about 75 to about 20,000 daltons.

The agent according to the invention may furthermore contain at least one vitamin, a provitamin, a vitamin precursor and/or one of the derivatives thereof as a conditioning substance. Preferred vitamins, provitamins and vitamin precursors according to the invention are those which are conventionally assigned to groups A, B, C, E, F and H.

Like the addition of glycerol and/or propylene glycol, the addition of panthenol increases the flexibility of the polymer film formed using the agent according to the invention.

The agents according to the invention may furthermore contain at least one plant extract, but also mono- or oligosaccharides and/or lipids as conditioning substance.

Oil bodies are furthermore suitable as a conditioning substance. Natural and synthetic cosmetic oil bodies include, for example, vegetable oils, liquid paraffin oils, isoparaffin oils and synthetic hydrocarbons and di-n-alkyl ethers having a total of between 12 to 36 C atoms, in particular 12 to 24 C atoms.

Ester oils, i.e. esters of $C_6$-$C_{30}$ fatty acids with $C_2$-$C_{30}$ fatty alcohols, preferably monoesters of the fatty acids with alcohols with 2 to 24 C atoms such as for example isopropyl myristate (Rilanit® IPM), isononanoic acid $C_{16-18}$ alkyl esters (Cetiol® SN), 2-ethylhexyl palmitate (Cegesoft® 24), stearic acid 2-ethylhexyl ester, (Cetiol® 868), cetyl oleate, glycerol tricaprylate, coco fatty alcohol caprate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are further preferred conditioning oil bodies.

Additional suitable conditioning substances are dicarboxylic acid esters, symmetrical, asymmetrical or cyclic esters of carbonic acid with fatty alcohols, trifatty acid esters of saturated and/or unsaturated linear and/or branched fatty acids with glycerol, or fatty acid partial glycerides, which should be understood to mean monoglycerides, diglycerides and the technical mixtures thereof.

With regard to cosmetic action, advantageous cosmetic agents have proven to be those in which the proportion by weight of the oil body in the total weight of the agent amounts to from about 0.01 to about 5.0 wt. %, preferably from about 0.02 to about 4.0 wt. % and in particular from about 0.05 to about 2.0 wt. %.

The following tables show the composition of some preferred cosmetic agents (details in wt. % relative to the total weight of the cosmetic agent unless otherwise stated).

|  | Formula 1 | Formula 2 | Formula 3 | Formula 4 | Formula 5 |
|---|---|---|---|---|---|
| Copolymer A | 0.05 to 10 | 0.1 to 7.0 | 0.2 to 5.0 | 0.4 | 1.7 |
| Copolymer B | 0.05 to 10 | 0.1 to 7.0 | 0.2 to 5.0 | 0.8 | 3.4 |
| Copolymer C | 0.1 to 8.0 | 0.2 to 6.0 | 0.4 to 4.0 | 0.8 | 2.7 |
| Water, misc. | ad 100 | ad 100 | ad 100 | ad 100 | ad 100 |
|  | Formula 6 | Formula 7 | Formula 8 | Formula 9 | Formula 10 |
| Copolymer A[1] | 0.05 to 10 | 0.1 to 7.0 | 0.2 to 5.0 | 0.4 | 2.7 |
| Copolymer B | 0.05 to 10 | 0.1 to 7.0 | 0.2 to 5.0 | 0.8 | 0.5 |
| Copolymer C | 0.1 to 8.0 | 0.2 to 6.0 | 0.4 to 4.0 | 0.8 | 2.7 |
| Water, misc. | ad 100 | ad 100 | ad 100 | ad 100 | ad 100 |
|  | Formula 11 | Formula 12 | Formula 13 | Formula 14 | Formula 15 |
| Copolymer A | 0.05 to 10 | 0.1 to 7.0 | 0.2 to 5.0 | 0.4 | 2.7 |
| Copolymer B[2] | 0.05 to 10 | 0.1 to 7.0 | 0.2 to 5.0 | 0.8 | 0.5 |
| Copolymer C | 0.1 to 8.0 | 0.2 to 6.0 | 0.4 to 4.0 | 0.8 | 2.7 |
| Water, misc. | ad 100 | ad 100 | ad 100 | ad 100 | ad 100 |
|  | Formula 16 | Formula 17 | Formula 18 | Formula 19 | Formula 20 |
| Copolymer A | 0.05 to 10 | 0.1 to 7.0 | 0.2 to 5.0 | 0.4 | 2.7 |
| Copolymer B | 0.05 to 10 | 0.1 to 7.0 | 0.2 to 5.0 | 0.8 | 0.5 |
| Copolymer C[3] | 0.1 to 8.0 | 0.2 to 6.0 | 0.4 to 4.0 | 0.8 | 2.7 |
| Water, misc. | ad 100 | ad 100 | ad 100 | ad 100 | ad 100 |
|  | Formula 21 | Formula 22 | Formula 23 | Formula 24 | Formula 25 |
| Copolymer A[1] | 0.05 to 10 | 0.1 to 7.0 | 0.2 to 5.0 | 0.4 | 2.7 |
| Copolymer B[2] | 0.05 to 10 | 0.1 to 7.0 | 0.2 to 5.0 | 0.8 | 0.5 |
| Copolymer C[3] | 0.1 to 8.0 | 0.2 to 6.0 | 0.4 to 4.0 | 0.8 | 2.7 |
| Water, misc. | ad 100 | ad 100 | ad 100 | ad 100 | ad 100 |
|  | Formula 26 | Formula 27 | Formula 28 | Formula 29 | Formula 30 |
| Copolymer A | 0.05 to 10 | 0.1 to 7.0 | 0.2 to 5.0 | 0.4 | 1.7 |
| Copolymer B | 0.05 to 10 | 0.1 to 7.0 | 0.2 to 5.0 | 0.8 | 3.4 |
| Copolymer C | 0.1 to 8.0 | 0.2 to 6.0 | 0.4 to 4.0 | 0.8 | 2.7 |
| Alkanolamine[4] | 80 to 100 | 90 to 100 | 95 to 100 | 98 | 98 |
| Water, misc. | ad 100 | ad 100 | ad 100 | ad 100 | ad 100 |
|  | Formula 31 | Formula 32 | Formula 33 | Formula 34 | Formula 35 |
| Copolymer A[1] | 0.05 to 10 | 0.1 to 7.0 | 0.2 to 5.0 | 0.4 | 2.7 |
| Copolymer B | 0.05 to 10 | 0.1 to 7.0 | 0.2 to 5.0 | 0.8 | 0.5 |
| Copolymer C | 0.1 to 8.0 | 0.2 to 6.0 | 0.4 to 4.0 | 0.8 | 2.7 |

-continued

| | | | | | |
|---|---|---|---|---|---|
| Alkanolamine[4] | 80 to 100 | 90 to 100 | 95 to 100 | 98 | 98 |
| Water, misc. | ad 100 | ad 100 | ad 100 | ad 100 | ad 100 |
| | Formula 36 | Formula 37 | Formula 38 | Formula 39 | Formula 40 |
| Copolymer A | 0.05 to 10 | 0.1 to 7.0 | 0.2 to 5.0 | 0.4 | 2.7 |
| Copolymer B[2] | 0.05 to 10 | 0.1 to 7.0 | 0.2 to 5.0 | 0.8 | 0.5 |
| Copolymer C | 0.1 to 8.0 | 0.2 to 6.0 | 0.4 to 4.0 | 0.8 | 2.7 |
| Alkanolamine[4] | 80 to 100 | 90 to 100 | 95 to 100 | 98 | 98 |
| Water, misc. | ad 100 | ad 100 | ad 100 | ad 100 | ad 100 |
| | Formula 41 | Formula 42 | Formula 43 | Formula 44 | Formula 45 |
| Copolymer A | 0.05 to 10 | 0.1 to 7.0 | 0.2 to 5.0 | 0.4 | 2.7 |
| Copolymer B | 0.05 to 10 | 0.1 to 7.0 | 0.2 to 5.0 | 0.8 | 0.5 |
| Copolymer C[3] | 0.1 to 8.0 | 0.2 to 6.0 | 0.4 to 4.0 | 0.8 | 2.7 |
| Alkanolamine[4] | 80 to 100 | 90 to 100 | 95 to 100 | 98 | 98 |
| Water, misc. | ad 100 | ad 100 | ad 100 | ad 100 | ad 100 |
| | Formula 46 | Formula 47 | Formula 48 | Formula 49 | Formula 50 |
| Copolymer A[1] | 0.05 to 10 | 0.1 to 7.0 | 0.2 to 5.0 | 0.4 | 2.7 |
| Copolymer B[2] | 0.05 to 10 | 0.1 to 7.0 | 0.2 to 5.0 | 0.8 | 0.5 |
| Copolymer C[3] | 0.1 to 8.0 | 0.2 to 6.0 | 0.4 to 4.0 | 0.8 | 2.7 |
| Alkanolamine[4] | 80 to 100 | 90 to 100 | 95 to 100 | 98 | 98 |
| Water, misc. | ad 100 | ad 100 | ad 100 | ad 100 | ad 100 |
| | Formula 51 | Formula 52 | Formula 53 | Formula 54 | Formula 55 |
| Copolymer A[1] | 0.05 to 10 | 0.1 to 7.0 | 0.2 to 5.0 | 0.4 | 2.7 |
| Copolymer B[2] | 0.05 to 10 | 0.1 to 7.0 | 0.2 to 5.0 | 0.8 | 0.5 |
| Copolymer C[3] | 0.1 to 8.0 | 0.2 to 6.0 | 0.4 to 4.0 | 0.8 | 2.7 |
| Alkyltrimethylammonium chloride | 0.05 to 3.0 | 0.1 to 2.0 | 0.2 to 1.0 | 0.5 | 0.3 |
| Water, misc. | ad 100 | ad 100 | ad 100 | ad 100 | ad 100 |
| | Formula 56 | Formula 57 | Formula 58 | Formula 59 | Formula 60 |
| Copolymer A[1] | 0.05 to 10 | 0.1 to 7.0 | 0.2 to 5.0 | 0.4 | 2.7 |
| Copolymer B[2] | 0.05 to 10 | 0.1 to 7.0 | 0.2 to 5.0 | 0.8 | 0.5 |
| Copolymer C[3] | 0.1 to 8.0 | 0.2 to 6.0 | 0.4 to 4.0 | 0.8 | 2.7 |
| Oil bodies | 0.01 to 5.0 | 0.02 to 4.0 | 0.05 to 2.0 | 0.1 | 0.1 |
| Water, misc. | ad 100 | ad 100 | ad 100 | ad 100 | ad 100 |
| | Formula 61 | Formula 62 | Formula 63 | Formula 64 | Formula 65 |
| Copolymer A[1] | 0.05 to 10 | 0.1 to 7.0 | 0.2 to 5.0 | 0.4 | 2.7 |
| Copolymer B[2] | 0.05 to 10 | 0.1 to 7.0 | 0.2 to 5.0 | 0.8 | 0.5 |
| Copolymer C[3] | 0.1 to 8.0 | 0.2 to 6.0 | 0.4 to 4.0 | 0.8 | 2.7 |
| Water | 40 to 99 | 50 to 98 | 60 to 95 | 97 | 92 |
| Misc. | ad 100 | ad 100 | ad 100 | ad 100 | ad 100 |

[1] Copolymer A, which consists in a proportion of at least about 90 wt. % and in particular of at least about 95 wt. % of the structural units (A1), (A2), (A3) and (A4), wherein
R1 in formula (A1) denotes a residue -CH(CH$_3$)CH$_2$— (OCH(CH$_3$)CH$_2$) x (O[CH$_2$]$_2$)$_y$OCH$_3$, in which x and y mutually independently have a value between 1 and 100;
R2 in formula (A2) denotes a residue -(CH$_2$)$_3$— N(CH$_3$)2;
one residue R3 denotes -CH$_2$CH$_3$ and one residue R3 in formula (A3) denotes H.
[2] Copolymer B, which consists in a proportion of at least about 90 wt. % and in particular of at least about 95 wt. % of the structural unit (B1), in which the residue R4 denotes -CH3.
[3] Copolymer C, which is formed in a proportion of at least about 90 wt. % and in particular of at least about 95 wt. % from at least two monomers C1, wherein the first monomer is selected from acrylic acid, methacrylic acid, methyl acrylate, methyl methacrylate, ethyl acrylate, ethyl methacrylate, propyl acrylate, propyl methacrylate, isopropyl acrylate and isopropyl methacrylate, and the second monomer is selected from stearyl acrylate and stearyl methacrylate, and
methacryloylethyl-N,N-dimethylamine oxide as monomer C2
[4] % of the quantity required for complete neutralization of copolymer A The agents according to the invention may be formulated in any forms conventional for cosmetic agents, for example in the form of solutions, which may be applied onto the hair as a hair lotion, pump or aerosol spray, in the form of creams, emulsions, waxes, gels or also surfactant-containing foaming solutions or other preparations which are suitable for application onto the hair. The agents according to the invention are preferably in liquid form, for example in the form of a spray or aerosol spray. In an alternative embodiment, these agents may however also assume gel or cream form, wherein transparent gels are more preferred.

As explained further above, in addition to the further active substances and auxiliary substances, the preferred aerosol sprays contain a propellant. Propellants (propellant gases) suitable according to the invention are propane, n-butane, iso-butane, dimethyl ether (DME), nitrogen, air, nitrous oxide, 1,1-difluoroethane, specifically both individually and in combination. Hydrophilic propellant gases, such as for example carbon dioxide, may advantageously be used for the purposes of the present invention if a small proportion of hydrophilic gases is selected and a lipophilic propellant gas (for example propane/butane) is present in excess. Dimethyl ether, propane, n-butane, iso-butane and mixtures of these propellant gases are more preferred. The use of propane/butane mixtures or isobutane is particularly preferred. Cosmetic agents which, relative to the total weight thereof, contain the propellant in a quantity of from about 2.0 to about 20 wt. %, preferably from about 4.0 to about 15 wt. % and more preferably from about 5.0 to about 10 wt. %, are preferred according to the invention.

The following table shows the composition of some preferred propellant-containing cosmetic agents. In this table the left-hand column ("formula x") refers in each case to one of the exemplary cosmetic compositions listed in the tables disclosed further above. The further columns two to seven ("propellant") in each case indicate the quantity of propellant added to the corresponding cosmetic composition. These indications in "wt. %" relate to the total weight of the cosmetic composition of the respective "formula x" without propellant.

In other words, a cosmetic preparation according to line 12, column 5 of the following table comprises a 20:1 mixture of the propellant-free cosmetic agent according to formula II with a propane/butane mixture.

|  | Propellant [wt. %] | | | | | |
| --- | --- | --- | --- | --- | --- | --- |
| Formula 1 | 2.0 to 10 | 5.0 | 2.0 to 10 P/B* | 5.0 P/B | 2.0 to 10 iB** | 5.0 iB |
| Formula 2 | 2.0 to 10 | 5.0 | 2.0 to 10 P/B* | 5.0 P/B | 2.0 to 10 iB** | 5.0 iB |
| Formula 3 | 2.0 to 10 | 5.0 | 2.0 to 10 P/B* | 5.0 P/B | 2.0 to 10 iB** | 5.0 iB |
| Formula 4 | 2.0 to 10 | 5.0 | 2.0 to 10 P/B* | 5.0 P/B | 2.0 to 10 iB** | 5.0 iB |
| Formula 5 | 2.0 to 10 | 5.0 | 2.0 to 10 P/B* | 5.0 P/B | 2.0 to 10 iB** | 5.0 iB |
| Formula 6 | 2.0 to 10 | 5.0 | 2.0 to 10 P/B* | 5.0 P/B | 2.0 to 10 iB** | 5.0 iB |
| Formula 7 | 2.0 to 10 | 5.0 | 2.0 to 10 P/B* | 5.0 P/B | 2.0 to 10 iB** | 5.0 iB |
| Formula 8 | 2.0 to 10 | 5.0 | 2.0 to 10 P/B* | 5.0 P/B | 2.0 to 10 iB** | 5.0 iB |
| Formula 9 | 2.0 to 10 | 5.0 | 2.0 to 10 P/B* | 5.0 P/B | 2.0 to 10 iB** | 5.0 iB |
| Formula 10 | 2.0 to 10 | 5.0 | 2.0 to 10 P/B* | 5.0 P/B | 2.0 to 10 iB** | 5.0 iB |
| Formula 11 | 2.0 to 10 | 5.0 | 2.0 to 10 P/B* | 5.0 P/B | 2.0 to 10 iB** | 5.0 iB |
| Formula 12 | 2.0 to 10 | 5.0 | 2.0 to 10 P/B* | 5.0 P/B | 2.0 to 10 iB** | 5.0 iB |
| Formula 13 | 2.0 to 10 | 5.0 | 2.0 to 10 P/B* | 5.0 P/B | 2.0 to 10 iB** | 5.0 iB |
| Formula 14 | 2.0 to 10 | 5.0 | 2.0 to 10 P/B* | 5.0 P/B | 2.0 to 10 iB** | 5.0 iB |
| Formula 15 | 2.0 to 10 | 5.0 | 2.0 to 10 P/B* | 5.0 P/B | 2.0 to 10 iB** | 5.0 iB |
| Formula 16 | 2.0 to 10 | 5.0 | 2.0 to 10 P/B* | 5.0 P/B | 2.0 to 10 iB** | 5.0 iB |
| Formula 17 | 2.0 to 10 | 5.0 | 2.0 to 10 P/B* | 5.0 P/B | 2.0 to 10 iB** | 5.0 iB |
| Formula 18 | 2.0 to 10 | 5.0 | 2.0 to 10 P/B* | 5.0 P/B | 2.0 to 10 iB** | 5.0 iB |
| Formula 19 | 2.0 to 10 | 5.0 | 2.0 to 10 P/B* | 5.0 P/B | 2.0 to 10 iB** | 5.0 iB |
| Formula 20 | 2.0 to 10 | 5.0 | 2.0 to 10 P/B* | 5.0 P/B | 2.0 to 10 iB** | 5.0 iB |
| Formula 21 | 2.0 to 10 | 5.0 | 2.0 to 10 P/B* | 5.0 P/B | 2.0 to 10 iB** | 5.0 iB |
| Formula 22 | 2.0 to 10 | 5.0 | 2.0 to 10 P/B* | 5.0 P/B | 2.0 to 10 iB** | 5.0 iB |
| Formula 23 | 2.0 to 10 | 5.0 | 2.0 to 10 P/B* | 5.0 P/B | 2.0 to 10 iB** | 5.0 iB |
| Formula 24 | 2.0 to 10 | 5.0 | 2.0 to 10 P/B* | 5.0 P/B | 2.0 to 10 iB** | 5.0 iB |
| Formula 25 | 2.0 to 10 | 5.0 | 2.0 to 10 P/B* | 5.0 P/B | 2.0 to 10 iB** | 5.0 iB |
| Formula 26 | 2.0 to 10 | 5.0 | 2.0 to 10 P/B* | 5.0 P/B | 2.0 to 10 iB** | 5.0 iB |
| Formula 27 | 2.0 to 10 | 5.0 | 2.0 to 10 P/B* | 5.0 P/B | 2.0 to 10 iB** | 5.0 iB |
| Formula 28 | 2.0 to 10 | 5.0 | 2.0 to 10 P/B* | 5.0 P/B | 2.0 to 10 iB** | 5.0 iB |
| Formula 29 | 2.0 to 10 | 5.0 | 2.0 to 10 P/B* | 5.0 P/B | 2.0 to 10 iB** | 5.0 iB |
| Formula 30 | 2.0 to 10 | 5.0 | 2.0 to 10 P/B* | 5.0 P/B | 2.0 to 10 iB** | 5.0 iB |
| Formula 31 | 2.0 to 10 | 5.0 | 2.0 to 10 P/B* | 5.0 P/B | 2.0 to 10 iB** | 5.0 iB |
| Formula 32 | 2.0 to 10 | 5.0 | 2.0 to 10 P/B* | 5.0 P/B | 2.0 to 10 iB** | 5.0 iB |
| Formula 33 | 2.0 to 10 | 5.0 | 2.0 to 10 P/B* | 5.0 P/B | 2.0 to 10 iB** | 5.0 iB |
| Formula 34 | 2.0 to 10 | 5.0 | 2.0 to 10 P/B* | 5.0 P/B | 2.0 to 10 iB** | 5.0 iB |
| Formula 35 | 2.0 to 10 | 5.0 | 2.0 to 10 P/B* | 5.0 P/B | 2.0 to 10 iB** | 5.0 iB |
| Formula 36 | 2.0 to 10 | 5.0 | 2.0 to 10 P/B* | 5.0 P/B | 2.0 to 10 iB** | 5.0 iB |
| Formula 37 | 2.0 to 10 | 5.0 | 2.0 to 10 P/B* | 5.0 P/B | 2.0 to 10 iB** | 5.0 iB |
| Formula 38 | 2.0 to 10 | 5.0 | 2.0 to 10 P/B* | 5.0 P/B | 2.0 to 10 iB** | 5.0 iB |
| Formula 39 | 2.0 to 10 | 5.0 | 2.0 to 10 P/B* | 5.0 P/B | 2.0 to 10 iB** | 5.0 iB |
| Formula 40 | 2.0 to 10 | 5.0 | 2.0 to 10 P/B* | 5.0 P/B | 2.0 to 10 iB** | 5.0 iB |
| Formula 41 | 2.0 to 10 | 5.0 | 2.0 to 10 P/B* | 5.0 P/B | 2.0 to 10 iB** | 5.0 iB |
| Formula 42 | 2.0 to 10 | 5.0 | 2.0 to 10 P/B* | 5.0 P/B | 2.0 to 10 iB** | 5.0 iB |
| Formula 43 | 2.0 to 10 | 5.0 | 2.0 to 10 P/B* | 5.0 P/B | 2.0 to 10 iB** | 5.0 iB |
| Formula 44 | 2.0 to 10 | 5.0 | 2.0 to 10 P/B* | 5.0 P/B | 2.0 to 10 iB** | 5.0 iB |
| Formula 45 | 2.0 to 10 | 5.0 | 2.0 to 10 P/B* | 5.0 P/B | 2.0 to 10 iB** | 5.0 iB |
| Formula 46 | 2.0 to 10 | 5.0 | 2.0 to 10 P/B* | 5.0 P/B | 2.0 to 10 iB** | 5.0 iB |
| Formula 47 | 2.0 to 10 | 5.0 | 2.0 to 10 P/B* | 5.0 P/B | 2.0 to 10 iB** | 5.0 iB |
| Formula 48 | 2.0 to 10 | 5.0 | 2.0 to 10 P/B* | 5.0 P/B | 2.0 to 10 iB** | 5.0 iB |
| Formula 49 | 2.0 to 10 | 5.0 | 2.0 to 10 P/B* | 5.0 P/B | 2.0 to 10 iB** | 5.0 iB |
| Formula 50 | 2.0 to 10 | 5.0 | 2.0 to 10 P/B* | 5.0 P/B | 2.0 to 10 iB** | 5.0 iB |
| Formula 51 | 2.0 to 10 | 5.0 | 2.0 to 10 P/B* | 5.0 P/B | 2.0 to 10 iB** | 5.0 iB |
| Formula 52 | 2.0 to 10 | 5.0 | 2.0 to 10 P/B* | 5.0 P/B | 2.0 to 10 iB** | 5.0 iB |
| Formula 53 | 2.0 to 10 | 5.0 | 2.0 to 10 P/B* | 5.0 P/B | 2.0 to 10 iB** | 5.0 iB |
| Formula 54 | 2.0 to 10 | 5.0 | 2.0 to 10 P/B* | 5.0 P/B | 2.0 to 10 iB** | 5.0 iB |
| Formula 55 | 2.0 to 10 | 5.0 | 2.0 to 10 P/B* | 5.0 P/B | 2.0 to 10 iB** | 5.0 iB |
| Formula 56 | 2.0 to 10 | 5.0 | 2.0 to 10 P/B* | 5.0 P/B | 2.0 to 10 iB** | 5.0 iB |
| Formula 57 | 2.0 to 10 | 5.0 | 2.0 to 10 P/B* | 5.0 P/B | 2.0 to 10 iB** | 5.0 iB |
| Formula 58 | 2.0 to 10 | 5.0 | 2.0 to 10 P/B* | 5.0 P/B | 2.0 to 10 iB** | 5.0 iB |
| Formula 59 | 2.0 to 10 | 5.0 | 2.0 to 10 P/B* | 5.0 P/B | 2.0 to 10 iB** | 5.0 iB |
| Formula 60 | 2.0 to 10 | 5.0 | 2.0 to 10 P/B* | 5.0 P/B | 2.0 to 10 iB** | 5.0 iB |
| Formula 61 | 2.0 to 10 | 5.0 | 2.0 to 10 P/B* | 5.0 P/B | 2.0 to 10 iB** | 5.0 iB |
| Formula 62 | 2.0 to 10 | 5.0 | 2.0 to 10 P/B* | 5.0 P/B | 2.0 to 10 iB** | 5.0 iB |
| Formula 63 | 2.0 to 10 | 5.0 | 2.0 to 10 P/B* | 5.0 P/B | 2.0 to 10 iB** | 5.0 iB |

-continued

| | Propellant [wt. %] | | | | | |
|---|---|---|---|---|---|---|
| Formula 64 | 2.0 to 10 | 5.0 | 2.0 to 10 P/B* | 5.0 P/B | 2.0 to 10 iB** | 5.0 iB |
| Formula 65 | 2.0 to 10 | 5.0 | 2.0 to 10 P/B* | 5.0 P/B | 2.0 to 10 iB** | 5.0 iB |

*P/B corresponds to a propane/butane mixture
**iB corresponds to isobutane

As explained above, the agents according to the invention have advantageous hair-fixing properties. The present application therefore also provides a method for temporarily deforming keratinic fibers, in which a composition according to the invention is applied onto the keratinic fibers. The present application also provides use of a cosmetic agent according to the invention for temporarily deforming keratinic fibers. As explained above, the agents according to the invention are distinguished in particular by improved hold in the case of temporary deformation of keratinic fibers. The present application therefore additionally provides the use of a cosmetic agent according to the invention to improve hold in the case of temporary deformation of keratinic fibers.

The invention claimed is:

1. A cosmetic agent, containing in a cosmetically acceptable carrier
a) at least one copolymer A with at least one structural unit (A1), at least one structural unit (A2), at least one structural unit (A3) and at least one structural unit (A4),

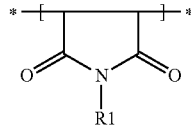
(A1)

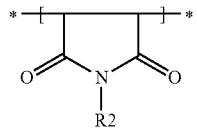
(A2)

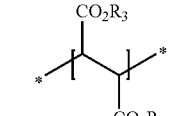
(A3)

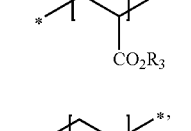
(A4)

wherein
R1 denotes an optionally heterofunctionalized alkyl residue;
R2 denotes an optionally heterofunctionalized alkyl residue differing from R1;
R3 denotes an optionally heterofunctionalized alkyl residue mutually independently differing from R1 and R2;
b) at least one copolymer B differing from copolymer A with at least one structural unit (B1)

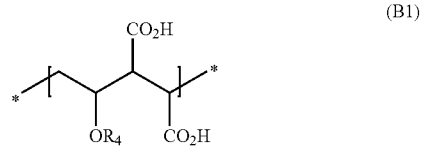
(B1)

wherein R4 denotes an optionally heterofunctionalized alkyl residue; and
c) at least one copolymer C differing from copolymer A and copolymer B, prepared from
at least one monomer C1 selected from acrylic acid, methacrylic acid, acrylic acid alkyl esters and methacrylic acid alkyl esters, and
at least one amphoteric monomer C2 selected from (meth)acryloyl alkyl amine oxides of formula C2-I

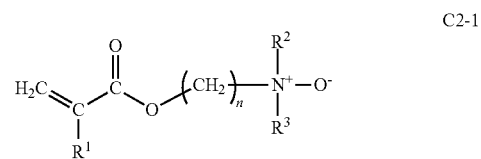
C2-I and (meth)acryloyl alkyl betaines of formula C2-II

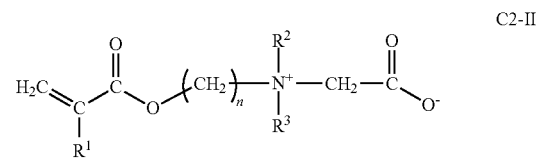
C2-II wherein in formula C2-I and in formula C2-II
R1 denotes H or $CH_3$,
R2 and R3 in each case mutually independently denote optionally branched $C_{1-10}$ alkyl, and
n denotes an integer from 1 to 20.

2. The cosmetic agent according to claim 1, characterized in that the
R1 in formula (A1) denotes a residue —$CH(CH_3)CH_2$—$(OCH(CH_3)CH_2)_x(O[CH_2]_z)_yOCH_3$, in which x and y mutually independently have a value between 1 and 100;
R2 in formula (A2) denotes a residue —$(CH_2)_3$—$N(CH_3)_2$;
one residue R3 denotes —$CH_2CH_3$ and one residue R3 in formula (A3) denotes H.

3. The cosmetic agent according to claim 1, characterized in that the proportion by weight of copolymer A in the total weight of the agent amounts to from about 0.05 to about 10 wt. %.

4. The cosmetic agent according to claim 1, characterized in that the proportion by weight of copolymer A in the total weight of the agent amounts to from about 0.1 to about 7.0 wt. %.

5. The cosmetic agent according to claim 1, characterized in that the proportion by weight of copolymer A in the total weight of the agent amounts to from about 0.2 to about 5.0 wt. %.

6. The cosmetic agent according to claim 1, characterized in that the residue R4 in formula (B1) denotes —CH$_3$.

7. The cosmetic agent according to claim 1, characterized in that the proportion by weight of copolymer B in the total weight of the agent amounts to from about 0.05 to about 10 wt. %.

8. The cosmetic agent according to claim 1, characterized in that the proportion by weight of copolymer B in the total weight of the agent amounts to from about 0.1 to about 7.0 wt. %.

9. The cosmetic agent according to claim 1, characterized in that the proportion by weight of copolymer B in the total weight of the agent amounts to from about 0.2 to about 5.0 wt. %.

10. The cosmetic agent according to claim 1, characterized in that the cosmetic agent furthermore contains at least one 1,2-diol.

11. The cosmetic agent according to claim 1, characterized in that the cosmetic agent furthermore contains 1,2-octanediol.

12. The cosmetic agent according to claim 1, characterized in that copolymer B is formed from
at least two monomers C1, wherein the first monomer is selected from acrylic acid, methacrylic acid, methyl acrylate, methyl methacrylate, ethyl acrylate, ethyl methacrylate, propyl acrylate, propyl methacrylate, isopropyl acrylate and isopropyl methacrylate, and the second monomer is selected from stearyl acrylate and stearyl methacrylate, and
methacryloyl ethyl amine oxide as monomer C2.

13. The cosmetic agent according to claim 1, characterized in that the proportion by weight of copolymer C in the total weight of the agent amounts to from about 0.1 to about 8.0 wt. %.

14. The cosmetic agent according to claim 1, characterized in that the proportion by weight of copolymer C in the total weight of the agent amounts to from about 0.2 to about 6.0 wt. %.

15. The cosmetic agent according to claim 1, characterized in that the proportion by weight of copolymer C in the total weight of the agent amounts to from about 0.4 to about 4.0 wt. %.

16. A method for temporarily deforming keratinic fibers comprising: providing a cosmetic agent, containing in a cosmetically acceptable carrier
a) at least one copolymer A with at least one structural unit (A1), at least one structural unit (A2), at least one structural unit (A3) and at least one structural unit (A4),

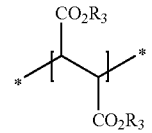

(A1)

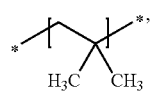

(A2)

-continued

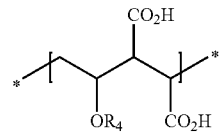

(A3)

(A4)

wherein
R1 denotes an optionally heterofunctionalized alkyl residue;
R2 denotes an optionally heterofunctionalized alkyl residue differing from R1;
R3 denotes an optionally heterofunctionalized alkyl residue mutually independently differing from R1 and R2;

b) at least one copolymer B differing from copolymer A with at least one structural unit (B1)

(B1)

wherein R4 denotes an optionally heterofunctionalized alkyl residue; and c) at least one copolymer C differing from copolymer A and copolymer B, prepared from
at least one monomer C1 selected from acrylic acid, methacrylic acid, acrylic acid alkyl esters and methacrylic acid alkyl esters, and
at least one amphoteric monomer C2 selected from (meth)acryloyl alkyl amine oxides of formula C2-I

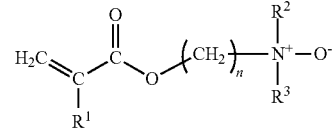

C2-I and (meth)acryloyl alkyl betaines of formula C2-II

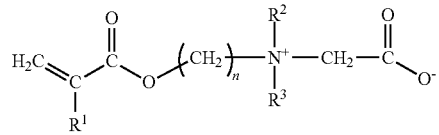

C2-II wherein in formula C2-I and in formula C2-II
R1 denotes H or CH$_3$,
R2 and R3 in each case mutually independently denote optionally branched C$_{1-10}$ alkyl, and
n denotes an integer from 1 to 20; and
applying the cosmetic agent onto the keratinic fibers.

* * * * *